(12) United States Patent
Haxha

(10) Patent No.: US 12,186,057 B2
(45) Date of Patent: Jan. 7, 2025

(54) CAPTURE OF PHYSIOLOGICAL DATA USING AN OPTICAL APPARATUS

(71) Applicant: Shyqyri Haxha, Bexley (GB)

(72) Inventor: Shyqyri Haxha, Bexley (GB)

( * ) Notice: Subject to any disclaimer, the term of this patent is extended or adjusted under 35 U.S.C. 154(b) by 0 days.

(21) Appl. No.: 18/712,993

(22) PCT Filed: Jul. 20, 2022

(86) PCT No.: PCT/GB2022/051873
§ 371 (c)(1),
(2) Date: May 23, 2024

(87) PCT Pub. No.: WO2023/094786
PCT Pub. Date: Jun. 1, 2023

(65) Prior Publication Data
US 2024/0335118 A1 Oct. 10, 2024

(30) Foreign Application Priority Data
Nov. 23, 2021 (GB) ..................... 2116875

(51) Int. Cl.
*A61B 5/00* (2006.01)
(52) U.S. Cl.
CPC .......... *A61B 5/0075* (2013.01); *A61B 5/6826* (2013.01); *A61B 5/7203* (2013.01); *A61B 5/7221* (2013.01); *A61B 5/7246* (2013.01); *A61B 5/7267* (2013.01); *A61B 2560/0238* (2013.01); *A61B 2562/043* (2013.01)

(58) Field of Classification Search
CPC ... A61B 5/0075; A61B 5/6826; A61B 5/7203; A61B 5/7221; A61B 5/7246; A61B 5/7267; A61B 2560/0238; A61B 2562/043
See application file for complete search history.

(56) References Cited

U.S. PATENT DOCUMENTS

2012/0253153 A1    10/2012    Trumble
2016/0331329 A1    11/2016    Hiroshima
(Continued)

OTHER PUBLICATIONS

International Search Report, PCT/GB2022/051873, dated Nov. 2022, Authorized Officer Gwenaëlle Dhervé, International filing date Jul. 20, 2022, Earliest priority date Nov. 23, 2021.
(Continued)

*Primary Examiner* — Scott M. Getzow
(74) *Attorney, Agent, or Firm* — Jose Gutman; Fleit Intellectual Property Law

(57) ABSTRACT

Method and apparatus for capturing physiological data, e.g. SpO2, comprises a wearable device such as a ring, carrying multiple light sources (LEDs) adapted to irradiate the wearer's finger with light, and multiple light sensors spaced apart across the device, e.g. circumferentially about the ring. Each light sensor is calibrated by determining an absolute value of light intensity received by the light sensor and using the absolute value to control the intensity of light outputted by the LED. This calibration process compensates for differing skin colors, tissues structures and environmental changes that affect the transmission or reflection characteristics of the tissues and/or performance of the light source or light detector. It also compensates for the differing tissue structures that lie between the light source and each of the light detectors that arise by virtue of each light detector's differing position relative to the light source.

17 Claims, 4 Drawing Sheets

(56) References Cited

U.S. PATENT DOCUMENTS

2020/0281477 A1 9/2020 Islam
2020/0315475 A1 10/2020 Huang

OTHER PUBLICATIONS

Written Opinion, PCT/GB2022/051873, dated Nov. 2022, Authorized Officer Gwenaëlle Dhervé, International filing date Jul. 20, 2022, Earliest priority date Nov. 23, 2021.
International Preliminary Report on Patentability, PCT/GB2022/051873, dated Jan. 19, 2024, Authorized Officer Gwenaëlle Dhervé, International filing date Jul. 20, 2022, Earliest priority date Nov. 23, 2021.

CAPTURE OF PHYSIOLOGICAL DATA USING AN OPTICAL APPARATUS

CROSS-REFERENCE TO RELATED APPLICATIONS

This application claims priority from and is related to the following prior application Patent Cooperation Treaty Application PCT/GB2022/052820, filed on Nov. 8, 2022, which claims priority from Great Britain Patent Application No. 2116047.8, filed on Nov. 8, 2021, and from Patent Cooperation Treaty Application PCT/GB2021/053234, filed on Dec. 9, 2021, and from Great Britain Patent Application No. 2207552.7, filed on May 23, 2022, and from Great Britain Patent Application No. 2207801.8, filed on May 26, 2022, and from Great Britain Patent Application No. 2212821.9, filed on Sep. 2, 2022. These prior applications, including the entirety of their written description and drawings, are collectively hereby incorporated by reference into the present application.

BACKGROUND

The present invention relates to an apparatus and method of capturing physiological data.

U.S. Pat. No. 10,918,289 describes a ring-shaped wearable device for measuring biometric data such as blood pressure and blood oxygenation, $SpO_2$. The ring device includes light sources that illuminate a digit of the wearer and photodiodes to measure biometric data from the received light. The device uses a motion sensor to detect motion of the user and uses this to remove noise from the signal.

Compared with traditional blood pressure monitors that comprise an inflatable cuff, a potential advantage of a device operating in the manner described in U.S. Pat. No. 10,918,289 is that it can be worn continuously allowing physiological measurements to be made over a long period, including whilst the wearer is participating in exercise.

However, in practice, it has proved difficult to reliably measure physiological signals using the technique described in U.S. Pat. No. 10,918,289 with sufficient accuracy that it can replace traditional measurement apparatus.

BRIEF SUMMARY

The present invention was conceived for the purpose of improving the accuracy of output signals from photodiodes used to detect physiological signals.

According to a first aspect of the invention there is provided a method of capturing physiological data from a mammalian subject comprising:

i) operating a first light source to irradiate tissue of the mammalian subject with light;

ii) using a plurality of light detectors to detect light from the light source that has transmitted through the tissue and/or reflected from the tissue, wherein each of the plurality of light detectors are adapted to provide an output signal indicative of the light detected; and wherein each of the plurality of light detectors are spaced apart from one another at known positions relative to the light source;

characterized in that the method comprises:

iii) selecting one of the light detectors from the plurality of light detectors, iv) using the output signal from the selected light detector to vary the intensity of light outputted from the light source to identify physiological data in the output signal and/or improve the quality of said identified physiological data;

v) if the presence of physiological data is identified, capturing the physiological data; and vi) selecting a next of the light detectors from the plurality of light detectors and repeating steps iii) to v).

This method compensates for differing skin color, tissues structures and environmental changes that affect the transmission or reflection characteristics of the tissues and/or performance of the light source or light detector. It also compensates for the differing tissue structures that lie between the light source and each of the light detectors that arise by virtue of each light detector's differing position relative to the light source.

The method may comprise measuring an absolute intensity value of the output signal and operating the light source to vary the intensity of light outputted from the light source to bring the absolute intensity value to within a range specified for the physiological data being captured The output signal includes a constant component, and a fluctuating component that is representative of the physiological data. The absolute intensity value is the sum of the constant and fluctuating components, corresponding to the intensity of light received at the photo detector. However, as the amplitude of the constant component is typically much greater than the maximum amplitude of the fluctuating component, the absolute intensity value is typically approximately equal to the value of the constant component.

Measuring different physiological data types will often require different absolute intensity values due to the need for the light to interact with different cells and different tissue structure configurations. As such, the method may include selecting a first physiological data type to measure from a plurality of measurable physiological data types, identifying a first absolute intensity value range for the selected physiological data type; and operating the light source to vary the intensity of light outputted in order that the absolute intensity value falls within the first absolute intensity value range.

The method may further comprise selecting a second physiological data type to measure from the plurality of physiological data types, identifying for the selected second physiological data type a second absolute intensity value range, said second absolute intensity value range being different from the first absolute intensity value range, and operating the light source to vary the intensity of light outputted in order that the absolute intensity value falls within the second absolute intensity value range.

The method may comprise performing a pattern recognition process on the fluctuating component of the output signal to identify a pattern that matches that of the physiological data.

To isolate the fluctuating component of the output signal from the constant component, the output signal may be passed through a filter, e.g. a high pass or band pass filter. The filtered signal may optionally be amplified before the pattern recognition process is carried out.

The method may comprise determining a pattern quality score for the identified pattern; setting a subrange of absolute intensity values for the output signal having a breadth based on the pattern quality score. The subrange of absolute intensity values being narrower that the absolute intensity value range for the relevant physiological data type.

The pattern quality score provides an indicator of the extent to which the pattern identified within the output signal matches the expected patterns for the physiological signal being captured, i.e. the degree of completeness of the data.

A lower pattern quality score is indicative that the current absolute intensity value of the output signal is far from the ideal absolute intensity value for capturing the physiological data and therefore a broader sub-range is selected. Conversely a higher pattern quality score suggests the current absolute intensity value of the output signal is near the ideal absolute intensity value and thus only a small adjustment is required.

The method may also include using the pattern quality score to set an interval size for changes in absolute intensity value within the subrange, and varying the intensity of the light outputted from the light source to alter the absolute intensity value by the interval size. This process may be repeated until a threshold pattern quality score is reached.

Typically, a larger interval size will be selected for lower pattern quality scores—and thus a larger interval size will be used where a broader subrange is selected. This way, relatively large adjustments to the absolute intensity value are made quickly when the pattern score is low, whilst finer adjustments are made when the pattern score is close to an acceptable level. This reduces the time required to adjust the absolute intensity value to reach the threshold pattern quality score.

Different physiological signal types may require irradiation of the tissue by different wavelengths of light. Furthermore, capture of certain physiological signals may be improved by using multiple wavelengths of light. As such, the light source may be operable to emit light in multiple non-overlapping wavebands, and the method comprises selecting a waveband to emit from the multiple non-overlapping wavebands based on the selected physiological data type. Where so, optimizing the absolute intensity value will also compensate for likely differences in transmission and reflection characteristics within the tissues for different wavelengths. For example, the light source may be operable to selectively emit light in multiple non-overlapping wavebands within wavelength range of 400 nm to 2600 nm.

Examples of physiological signals that may be measured include one or more of blood pressure, heart rate, oxygen saturation (spO2), blood glucose. Other examples include variables commonly identified in a full blood count such as, for example, one or more of: haemoglobin concentration, white blood cell count, red blood cell count, platelet count, volume % of red blood cells, red blood indices, white blood cell differential. Further, the respiratory rate may be measured as a derivative of the heart rate. The physiological signal(s) may include one or more variables associated with other body fluids such as sweat, for example sweat rate and mineral composition of sweat; and composition and changes in volume of interstitial fluids.

Another application of the device is to identify the reduction in blood flow, e.g. through measuring blood oxygen saturation level to identify necrotise of body tissue, e.g. in the extremities of the limbs such as for example, as a consequence of diabetes.

The invention may also be described in terms of apparatus, and thus according to another aspect of the invention there is provided apparatus for capturing physiological data from a mammalian subject comprising a light source for irradiate human tissue with light a plurality of light detectors to detect light from the light source that has transmitted through the tissue and/or reflected from the tissue, wherein each of the plurality of light detectors are spaced apart from one another at known positions relative to the light source; and a control and process means (e.g. control and processing circuitry) adapted to:

select one of the light detectors from the plurality of light detectors, ii) use the output signal from the selected light detector to vary the intensity of light outputted from the light source to identify physiological data in the output signal and/or improve the quality of said identified physiological data;

iii) if the presence of physiological data is determined, capture the physiological data; and iv) selecting a next of the light detectors from the plurality of light detectors and repeating steps i) to iii).

The apparatus may take the form of or comprise a ring, e.g. a metallic or rigid plastic ring. The apparatus may comprise a ring-shaped wearable device. The ring may be sized to be retained over the digit of a human hand. Alternatively, it may take other forms, e.g. an adhesive patch or mounted to or forming part of a belt, strap or inflatable cuff. These other forms allow the device to be retained against the skin at different locations about the body, e.g. leg, foot, arm or torso.

The above-described apparatus and/or method maybe adapted to capture physiological data from a human.

BRIEF DESCRIPTION OF THE DRAWINGS

The accompanying figures in which like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which.

DETAILED DESCRIPTION

As required, detailed embodiments are disclosed herein; however, it is to be understood that the disclosed embodiments are merely examples and that the devices and methods described herein can be embodied in various forms. Therefore, specific structural and functional details disclosed herein are not to be interpreted as limiting, but merely as a basis for the claims and as a representative basis for teaching one of ordinary skill in the art to variously employ the disclosed subject matter in virtually any appropriately detailed structure and function. Further, the terms and phrases used herein are not intended to be limiting, but rather, to provide an understandable description. Additionally, unless otherwise specifically expressed or clearly understood from the context of use, a term as used herein describes the singular and/or the plural of that term.

The terms "a" or "an", as used herein, are defined as one or more than one. The term "plurality", as used herein, is defined as two or more than two. The term "another", as used herein, is defined as at least a second or more. The terms "including" and "having," as used herein, are defined as comprising i.e., open language. The term "coupled," as used herein, is defined as "connected," although not necessarily directly, and not necessarily mechanically.

It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

Figure 1:
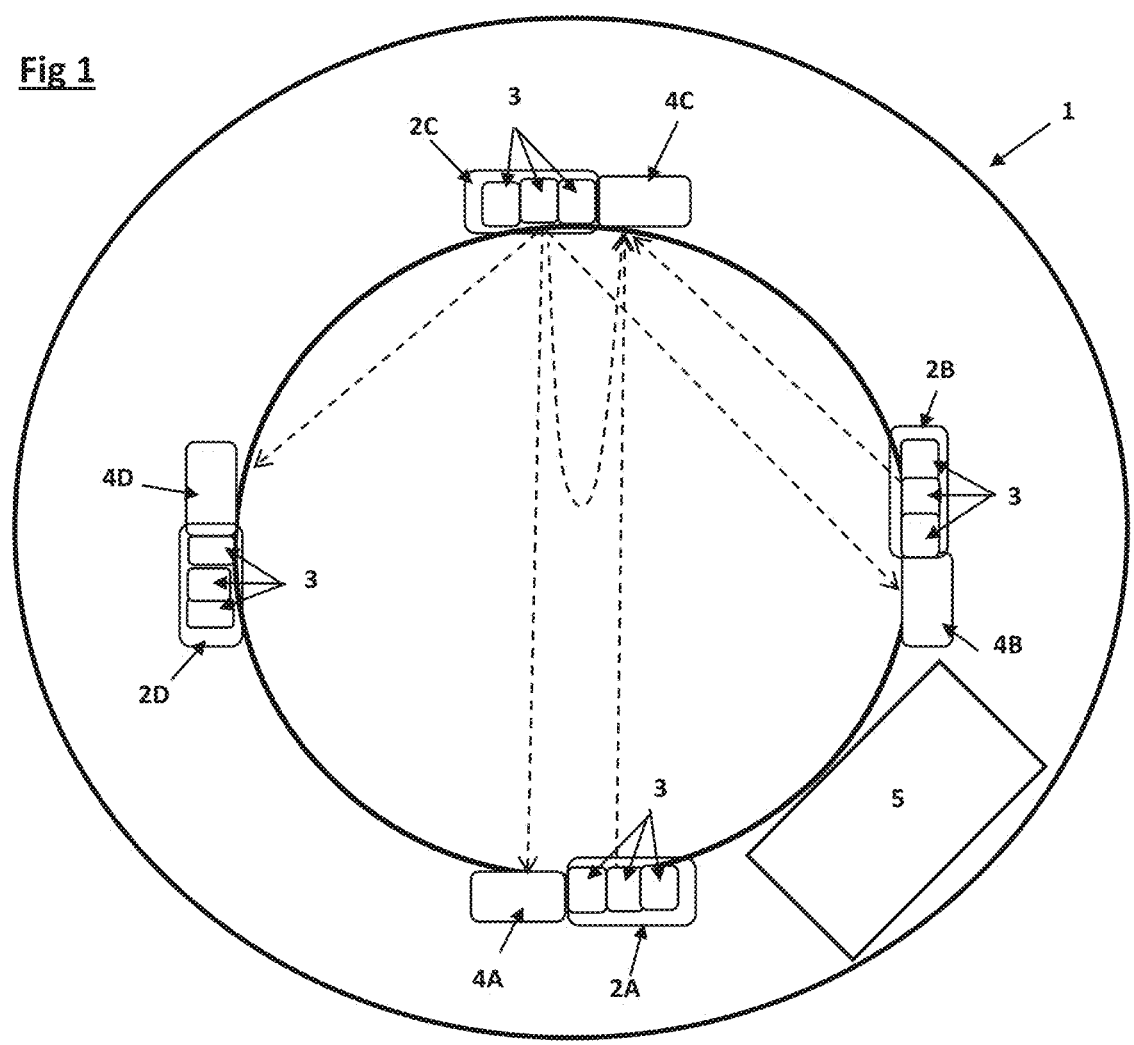
FIG. 1 is a schematic of a ring-shaped wearable device incorporating apparatus for detecting and capturing physiological signals.

With reference to FIG. 1 there is shown a ring-shaped wearable device 1 incorporating apparatus for detecting and recording physiological data. The device is sized to fit over and be retained on the digit of the hand or foot a person whose physiological data is to be captured.

The body of the device may be comprised of metal, plastic or any other material or combination of materials able to provide a suitable support. The choice of materials will depend on the expected purpose and/or the desired aesthetic of the device. For example, in one embodiment the device may be metallic in order to resemble a traditional wedding band. Alternatively, the body of the device may be comprised from an elastic material to allow the device to stretch over a digit or other body part, e.g. around the torso and be retained securely thereto.

Alternatively, device may be adapted to collect physiological data from other types of mammals—e.g. one or more of other primates, equines, canines, felines and bovines—in which case the device will be sized and shaped to be appropriate to the body part it will be retained against.

The device 1 comprises multiple light emitting diode (LEDs) devices 2A-2D that are spaced circumferentially about the inner facing side of the device to irradiate the tissue of the digit from all sides.

The example illustrates four LED devices 2 though the number may be as few as two or more than four.

Each LED device 2 comprises multiple LED elements 3, each element adapted to emit light within a different non-overlapping band within the infrared and/or visible spectrum, e.g. 400 nm-2600 nm. In the present example each LED device 2 comprises three LED elements 3 to emit light in three different non-overlapping bands within the 400 nm-2600 nm range The following example wavelengths suitable for identifying a variety of different physiological variables:
Optical Based Non-invasive Glucose Monitoring Sensor Prototype; Shyqyri Haxha; IEEE Volume 8, Number 6, December 2016;
A Novel Art of Continuous Non-invasive Blood Pressure Measurement; Jürgen Fortin NATURE COMMUNICATIONS (2021) 12:1387 https://doi.org/10.1038/s41467-021-21271-8.
Pulse Oximetry Optical Sensor Using Oxygen Bound Haemoglobin Z. J. V Cohen, Vol. 24, No. 9; OPTICS EXPRESS 10115 2 May 2016
Continuous Non-invasive Hemoglobin Monitoring: The Standard Of Care And Future Impact; Gerald J. Kost Crit Care Med. 2011 October; 39 (10): 2369-2371. doi: 10.1097/CCM.0b013e3182266013
A precise non-invasive blood glucose measurement system using NIR spectroscopy and Huber's regression model. Jain, P.; Maddila, R.; Joshi, A. M. Opt. Quantum Electron. 2019, 51, 51.

The device 1 also comprises multiple photo diode light detectors (PDs) 4A-4D spaced circumferentially about the ring. Their detecting apertures are arranged to face inwards towards the digit to detect light emitted from the LEDs 2 that has transmitted and/or reflected from the tissue of the digit.

Figure 2:
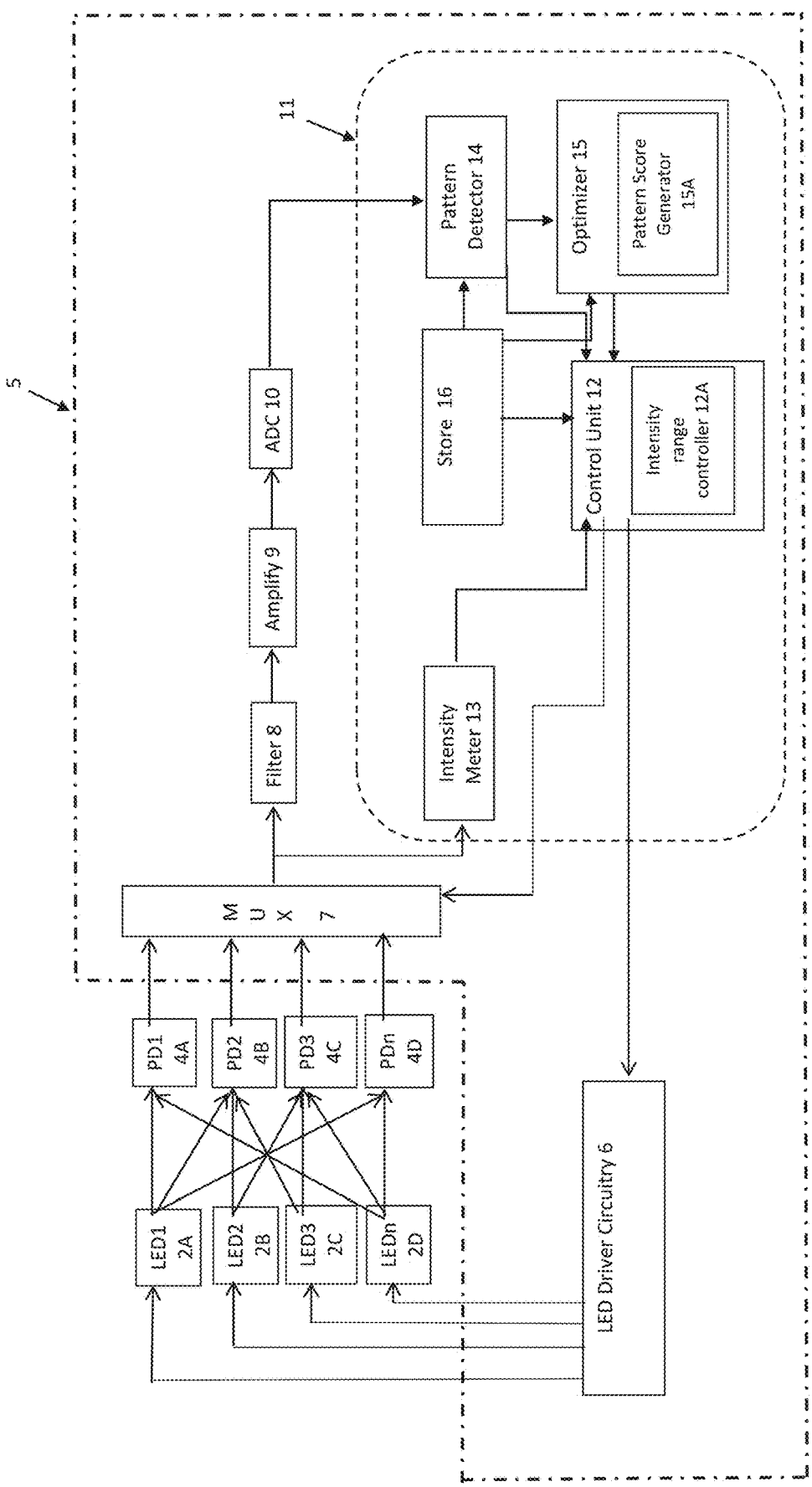
FIG. 2 is a schematic of the apparatus for detecting and capturing physiological signals.

With reference also to FIG. 2, in addition to the LEDs 2 and PDs 4, the apparatus also includes control and processing circuitry 5 which includes LED driver circuitry 6, a multiplexer 7, electrical filter 8, amplifier 9, analogue to digital converter (ADC) 10, and a processor 11.

Optionally, the device 1 may also include a user interface (not shown), e.g. one or more outward facing LEDs, to communicate an operating state of the device to the wearer and/or error codes.

The processor 11 comprises one or more processors communicatively coupled with computer readable memory adapted to run software to implement the functions of: a control unit 12, intensity meter 13, pattern detector 14, pattern optimizer 15 including a pattern score generator 15A, and a store 16.

The store holds minimum and maximum absolute intensity values for different physiological data types; sub range parameters associated with different pattern quality scores for each different physiological data type; and a library of pattern parameters for different physiological signals.

Figure 3:
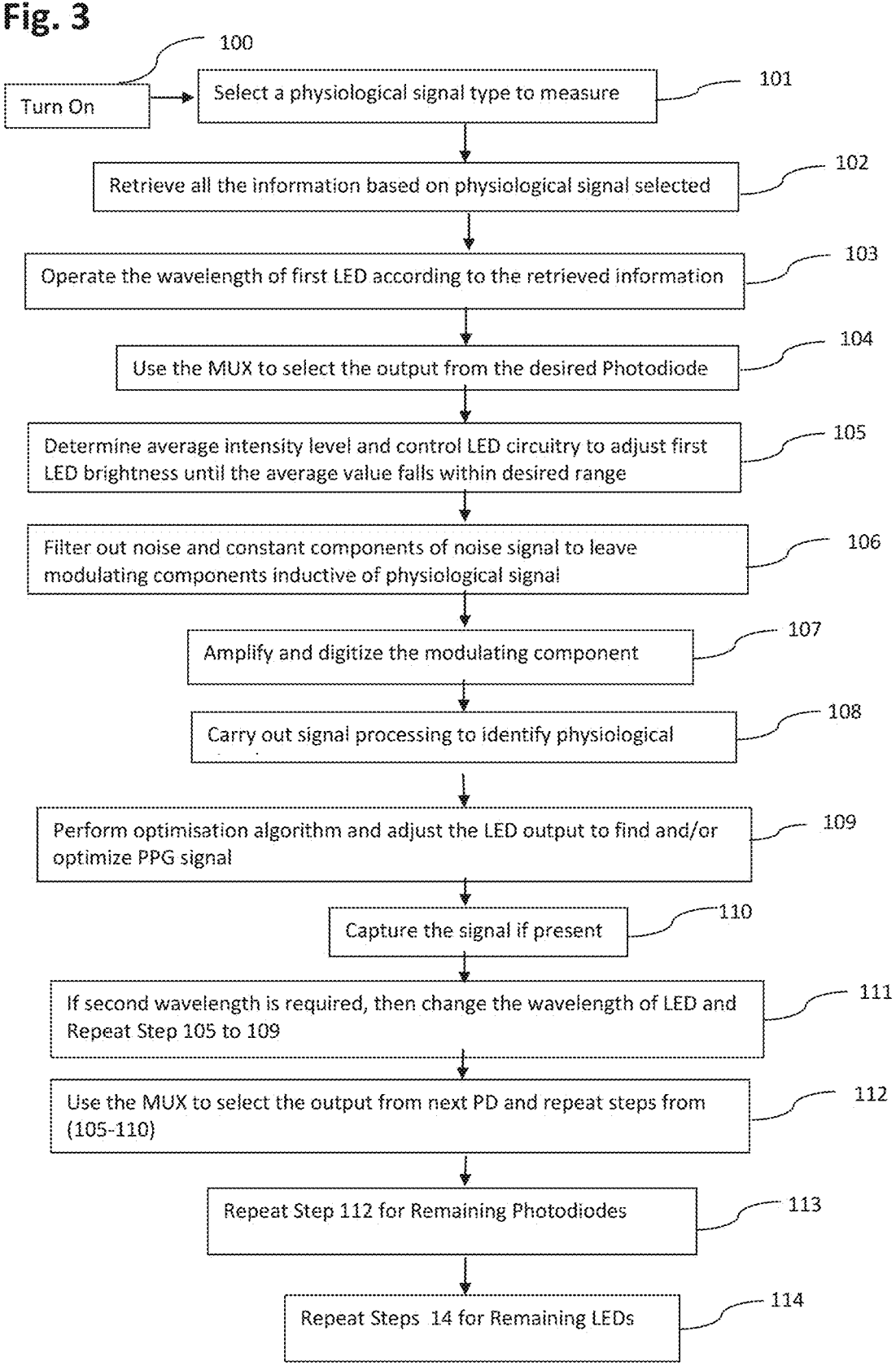
FIG. 3 illustrates process steps performed by the apparatus of FIG. 2.

The apparatus is configured to operate according to the algorithm described with reference to FIG. 3.

The system is initialized (100). The control unit 12 selects a first physiological signal type to be measured and recorded from a selection of measurable physiological signals. (101).

Information associated with the first physiological data type is retrieved from the store 16 (102). The information includes, wavelength, absolute intensity range values; pattern data; and sub-range data associated with pattern quality scores.

The control unit 12 controls the LED driver 6 to switch on a first LED element 3 of first LED device 2A to illuminate the tissue of the wearer's finger (103).

Light from the LED element 2A is partially transmitted and reflected by the tissue of the digit. Portions of said transmitted or reflected light are received at one or more (possibly all) of the photodiodes 4. As the light received at each photodiode 4 has a different path through the digit, the absolute value of the signal at each photodiode 4 will differ.

Additionally, because of the different paths, the light received at certain photodiodes may carry a stronger and/or better-quality representation of the selected physiological data than others. This may change over time, for example as a result of relative movement between the device 1 and the digit.

The control unit 12 operates the mux 7 to select one photodiode 4A of the multiple photodiodes 4 from which to receive an output signal (104).

The output signal from the selected photodiode 4A is received by the intensity meter 13 which outputs, to the control unit 12, an absolute intensity value indicative of the absolute intensity of light received at the photodiode.

The control unit 12 is adapted to receive the absolute intensity value, compare this with the absolute intensity value range retrieved from the store 16 for the selected physiological data type, and in response control the LED driver 6 to control, i.e. alter where necessary, the intensity of light emitted by the first LED element 3 of the first LED device 2A, until the absolute intensity value as determined by the intensity meter 13, falls within the absolute intensity value range (105).

The absolute intensity value is likely to fluctuate, in part because it may include a modulating component attributable to the physiological signal, though this is only likely to cause small fluctuations, but also because of noise, e.g. attributed to the output characteristics of the LED itself but also environmental factors, e.g. because of movement of the wearer, changes in ambient light, temperature. As such the control unit 12 may be adapted to alter the intensity of the LED 2 based on an average absolute intensity value.

The output from the mux 7 is also inputted to a band pass filter 8 that removes the constant (DC) component of the output signal (106) from the selected photodiode 4 to leave the varying component indicative of the physiological signals to be measured (108). The variable component output is amplified by amplifier 9 before being digitized by ADC 10 and inputted to the pattern detector 14 (107).

The pattern detector 14 is adapted to carry out signal processing on the digitized signal received from ADC 10 to identify the presence of physiological signals of the type selected at 101. The output of the pattern detector 14 may be a portion of the signal that matches or contains a pattern conforming to the selected physiological data or an indicator that no pattern has been detected.

The output from the pattern detector 14 is received by the pattern optimizer 15 which performs an optimization algorithm as described below, with reference to FIG. 4, to vary the intensity of the LED element 3 to find a pattern or optimize the quality of an identified pattern (109).

Once a pattern that meets the quality threshold is identified, a sample of the pattern is recorded in store 16 and/or may be transmitted, e.g. wirelessly, to a remote system. (110)

If illumination with a second wavelength is required to obtain further patterns for the selected physiological data type, the control unit 12 controls the LED driver 6 to operate the second LED element 3B of the first LED device 2A to illuminate the tissue of the wearer's finger with the second wavelength and steps 105-110 repeated (111).

If applicable, step 111 may be repeated to operate third element 3C, for a third wavelength.

Thereafter, the control unit 12 operates the mux 7 to select the second photodiode receiver 4B. Steps 105-111 are repeated to capture physiological signals from the output signals of the second photodiode receiver 4B. This is repeated for each of the photodiodes 4D.

Figure 4:
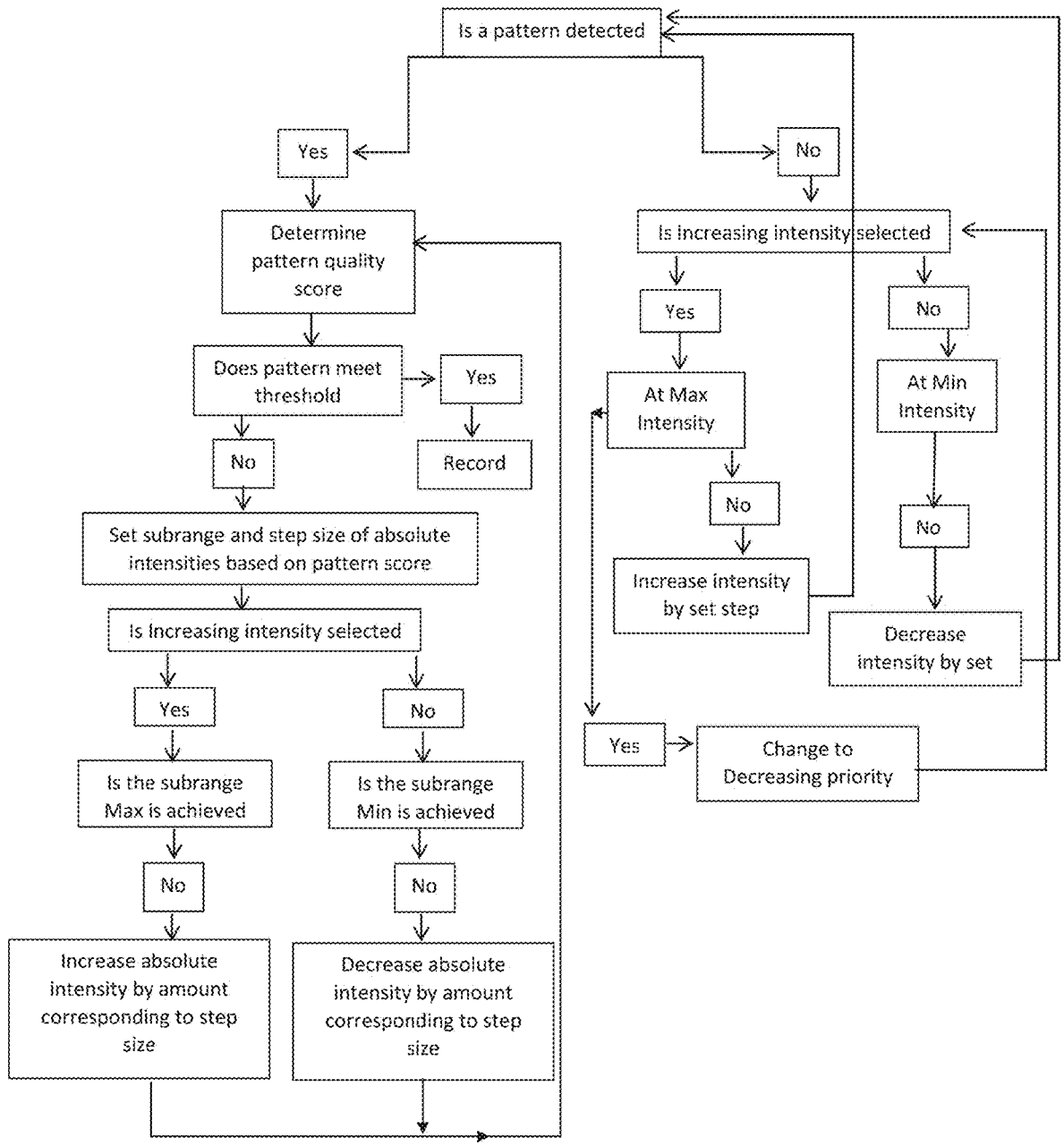
FIG. 4 illustrates process steps for pattern detection and optimizing pattern quality.

With reference to FIG. 4, the pattern detector 14 carries out one or more signal processing steps, e.g. cross correlation and/or fast Fourier transform to determine the presence of a signal within the output from the ADC 10 that matches one or patterns held in the store 16 that correspond to those having a known association with the selected physiological data type.

With reference to the process illustrated on the right-hand side of FIG. 4, if no pattern is detected by the pattern detector 14, a 'no pattern' signal is transmitted to the intensity range controller 12A. In response, if the controller 12 is set in an 'increase intensity state' and the absolute intensity value of the output signal is not at a maximum value within the range, the controller 12A controls the LED driver circuitry 6 to increase the intensity of the LED 3 until the absolute signal value increases by an incremental amount and awaits for a further 'no pattern' signal from the pattern detector 14. This is repeated until the maximum intensity within the range is reached or a pattern is detected.

If the maximum absolute intensity value is reached and still no pattern is detected, the control unit 12A switches to a 'decreasing intensity state' and decreases the absolute intensity value to a set increment below the initial intensity value, and then further decreases the absolute value by the increment until the minimum absolute intensity value of a pattern is reached.

If no pattern is found, the controller unit 12 operates the mux 7 to switch to a different photodiode 4.

Note that this process assumes that the initial absolute intensity value lies between the max and min values for that range. If the initial absolute value is at the min or max value then only an increasing or decreasing incrementation process needs to be used.

With reference to the left-hand process flow in FIG. 4, if a pattern is found, characteristics of the output signal that are determined to match the pattern are passed to the pattern score generator 15A which determines from this input, a pattern quality score.

The optimizer 15 determines whether the pattern score outputted from the pattern score generator 15A meets a threshold quality score. If yes, then the output signal from the ADC 10 is captured, e.g. passed to and recorded in the store 16.

If the pattern quality score does not meet the threshold, the optimizer 15 sets a sub-range of absolute intensity values centered on the current absolute intensity value and having a breadth that is based on the pattern score. The optimizer also sets an interval size for changes in the absolute intensity value within the sub-range. The interval size is dependent on the breadth of the sub-range, a broader sub-range has a larger interval size so that the whole breadth of the sub-range can be scanned quickly.

In response to a lower quality score, the optimizer sets a broader sub-range and a larger interval size, conversely in response to a higher quality score, indicative that only a small change in absolute intensity is needed to reach the threshold, the optimizer sets a narrower sub-range with a smaller interval size.

The sub-range and interval size information determined by the optimizer 15 is passed to the control unit 12, which in response alters the intensity of the LED element 3 to increase or decrease the absolute intensity value based on received sub-range and interval information from the optimizer 15 until a threshold pattern score is reached.

The pattern score generator uses a machine learning model adapted to receive the output of the ADC 10 as an input and that has been trained to identify the sought for physiological signal and to output a confidence level that the input signal comprises all expected features within the physiological signal. Examples of suitable machine learning models for the purpose may use, for example, linear regression, convolutional neural networks and Long short-term memory (LSTM architecture).

The identified physiological signal is processed to determine physiological variable values. The processing steps required will depend on the physiological variable being measured. IoT Health Monitoring Device of Oxygen Saturation (SpO2) and Heart Rate Level; OY Tham; 2020 1st International Conference on Information Technology, Advanced Mechanical and Electrical Engineering (ICITAMEE). https://www.researchgate.net/publication/352264532_IoT_Health_Monitoring_Device_of_Oxygen_Saturation_SpO2_and_Heart_Rate_Level describes example processing steps to determine SpO2 and heart rate.

In alternative embodiments, the device may be sized differently and/or take different forms. For example, rather than comprising a metal ring as a mounting structure, the device be comprised from a strip or loop of fabric or elastic material. The device may be sized to fit around another body part, e.g. leg, arm or chest. Alternatively, the device may take, for example, the form of a patch adapted to adhere or otherwise lie against the skin. It is not necessary, in all embodiments, for the device to extend circumferentially around the body part it is mounted against.

The Abstract is provided with the understanding that it is not intended be used to interpret or limit the scope or meaning of the claims. In addition, in the foregoing Detailed Description, various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The corresponding structures, materials, acts, and equivalents of all means or step plus function elements in the claims below are intended to include any structure, material, or act for performing the function in combination with other claimed elements as specifically claimed. The description herein has been presented for purposes of illustration and description, but is not intended to be exhaustive or limited to the examples in the form disclosed. Many modifications and variations will be apparent to those of ordinary skill in the art without departing from the scope of the examples presented or claimed. The disclosed embodiments were chosen and described in order to explain the principles of the embodiments and the practical application, and to enable others of ordinary skill in the art to understand the various embodiments with various modifications as are suited to the particular use contemplated. It is intended that the appended claims below cover any and all such applications, modifications, and variations within the scope of the embodiments.

Although specific embodiments of the subject matter have been disclosed, those having ordinary skill in the art will understand that changes can be made to the specific embodiments without departing from the scope of the disclosed subject matter. The scope of the disclosure is not to be restricted, therefore, to the specific embodiments, and it is intended that the appended claims cover any and all such applications, modifications, and embodiments within the scope of the present disclosure.

What is claimed is:

1. A method of capturing physiological data from a mammalian subject comprising:
   i) operating a light source to irradiate tissue of the mammalian subject with light;
   ii) using a plurality of light detectors to detect light from the light source that has transmitted through the tissue and/or reflected from the tissue, wherein each of the plurality of light detectors are adapted to provide an output signal indicative of the light detected; and wherein each of the plurality of light detectors are spaced apart from one another at known positions relative to the light source;
   characterized in that the method comprises:
   iii) selecting one of the light detectors from the plurality of light detectors,
   iv) using the output signal from the selected light detector to vary the intensity of light outputted from the light source to identify physiological data in the output signal and/or improve the quality of said identified physiological data;
   v) if the presence of physiological data is identified, capturing the physiological data; and
   vi) selecting a next of the light detectors from the plurality of light detectors and repeating steps iii) to v); and
   characterized in iv) comprises measuring an absolute intensity value of the output signal and operating the light source to vary the intensity of light outputted from the light source to bring the absolute intensity value to within a range specified for the physiological data being captured.

2. A method of taking physiological measurements according to claim 1, comprising:
   selecting a first physiological data type to measure from a plurality of measurable physiological data types,
   identifying a first absolute intensity value range for the selected physiological data type; and
   operating the light source to vary the intensity of light outputted in order that the absolute intensity value falls within the first absolute intensity value range.

3. A method according to claim 2, comprising:
   selecting a further physiological data type to measure from the plurality of physiological data types;
   identifying for the selected second physiological data type a second absolute intensity value range, said second absolute intensity value range being different from the first absolute intensity value range; and
   operating the light source to vary the intensity of light outputted in order that the absolute intensity value falls within the second absolute intensity value range.

4. A method according to claim 2, wherein the light source is operable to emit light in multiple non-overlapping wavebands, and the method comprises:
   selecting a first waveband to emit from the multiple non-overlapping wavebands based on the selected physiological data type to be measured.

5. A method according to according to claim 1, comprising:
   performing a pattern recognition process on a fluctuating component of the outputted signal to identify a pattern that matches the physiological data.

6. A method according to claim 5, comprising:
   determining a pattern quality score for the identified pattern; and varying the intensity of light outputted from the light source to improve the pattern quality score.

7. A method according to claim 6, comprising:
   using the pattern quality score to set a subrange of absolute intensity values for the first output signal; and
   varying the intensity of light outputted from the light source to vary the absolute intensity value of the output signal to fall within the subrange to improve the pattern quality score.

8. A method according to claim 7, wherein the absolute intensity value of the output signal is altered incrementally by an increment size, and that the value of the increment size is set based on a breadth of the set subrange.

9. A method according to claim 1, wherein the physiological data comprises one or more of blood pressure, heart rate, oxygen saturation (spO2), blood glucose and haemoglobin level.

10. An apparatus for capturing physiological data from a mammalian subject, comprising:
a light source to irradiate human tissue with light;
a plurality of light detectors to detect light from the light source that has transmitted through the tissue and/or reflected from the tissue, wherein each of the plurality of light detectors are spaced apart from one another at known positions relative to the light source; and
a controller, in response to executing software instructions, performing the following method:
  i) select one of the light detectors from the plurality of light detectors,
  ii) using an output signal from the selected light detector to vary the intensity of light outputted from the light source to identify physiological data in the output signal and/or improve the quality of said identified physiological data;
  iii) if the presence of physiological data is determined, capture the physiological data; and
  iv) select a next of the light detectors from the plurality of light detectors and repeating steps i) to iii); and
wherein ii) comprises measuring an absolute intensity value of the output signal and operating the light source to vary the intensity of light outputted from the light source to bring the absolute intensity value to within a range specified for the physiological data being captured that is held within a store of the apparatus.

11. The apparatus according to claim 10, wherein the controller, in response to executing software instructions, performing the following method:
selecting a first physiological data type to measure from a plurality of measurable physiological data types, held within a store of the apparatus identifying a first absolute intensity value range for the selected physiological data type; and
operating the light source to vary the intensity of light outputted in order that the absolute intensity value falls within the first absolute intensity value range.

12. The apparatus according to claim 11, wherein the controller, in response to executing software instructions, performing the following method:
selecting a second physiological data type held within a store of the apparatus to measure from the plurality of physiological data types;
identifying for the selected second physiological data type a second absolute intensity value range, said second absolute intensity value range being different from the first absolute intensity value range; and
operating the light source to vary the intensity of light outputted in order that the absolute intensity value falls within the second absolute intensity value range.

13. The apparatus according to claim 11, wherein the light source is operable to emit light in multiple non-overlapping wavebands, and the controller, in response to executing software instructions, performing the following method:
select a first waveband to emit from the multiple non-overlapping wavebands based on the selected physiological data type to be measured.

14. The apparatus according to claim 10, wherein the controller, in response to executing software instructions, performing the following method:
a pattern recognition process on a fluctuating component of the outputted signal to identify a pattern that matches the physiological data.

15. The apparatus according to claim 14, wherein the controller, in response to executing software instructions, performing the following method:
determining a pattern quality score for the identified pattern; and
varying the intensity of light outputted from the light source to improve the pattern quality score.

16. The apparatus according to claim 10, wherein the controller, in response to executing software instructions, performing the following method:
use the pattern quality score to set a subrange of absolute intensity values for the first output signal; and
varying the intensity of light outputted from the light source to vary the absolute intensity value of the output signal to fall within the subrange to improve the pattern quality score.

17. The apparatus according to claim 16, wherein the controller, in response to executing software instructions, performing the following method:
alter the absolute intensity value of the output signal incrementally by an increment size, and that the value of the increment size is set based on a breadth of the set subrange.

* * * * *